(12) United States Patent
Kamins et al.

(10) Patent No.: US 7,592,679 B1
(45) Date of Patent: Sep. 22, 2009

(54) SENSOR AND METHOD FOR MAKING THE SAME

(75) Inventors: Theodore I. Kamins, Palo Alto, CA (US); Philip J. Kuekes, Palo Alto, CA (US); Carrie L. Donley, Chapel Hill, NC (US); Jason J. Blackstock, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 474 days.

(21) Appl. No.: 11/583,648

(22) Filed: Oct. 19, 2006

(51) Int. Cl.
*H01L 29/78* (2006.01)

(52) U.S. Cl. ................ 257/414; 977/762; 977/765

(58) Field of Classification Search .......... 257/414; 977/762, 765
See application file for complete search history.

(56) References Cited

U.S. PATENT DOCUMENTS 7,312,155 B2 * 12/2007 Dubin et al. ............ 438/694

2005/0133476 A1    6/2005 Islam et al.

OTHER PUBLICATIONS

Islam, M. S. et al., "A novel interconnection technique for manufacturing nanowire devices," Appl. Phys. A, vol. 80, 2005, pp. 1133-1140.

Islam, M. S. et al., "Ultrahigh-density silicon nanobridges formed between two vertical silicon surfaces," Nanotechnology, vol. 15, 2004, pp. L5-L8.

* cited by examiner

*Primary Examiner*—Douglas M Menz

(57) ABSTRACT

A sensor includes at least two electrodes, and at least one nanowire extending substantially laterally between the electrodes. The at least one nanowire has at least two segments with a junction or connection formed therebetween. A sensing material changeable between at least two states is positioned adjacent to the junction or connection, and adjacent to at least a portion of each of the segments.

15 Claims, 1 Drawing Sheet

SENSOR AND METHOD FOR MAKING THE SAME

STATEMENT REGARDING FEDERALLY SPONSORED RESEARCH OR DEVELOPMENT

This invention was made in the course of research partially supported by the Defense Advanced Research Projects Agency, Agreement No. HR0011-05-3-0001. The U.S. government has certain rights in the invention.

BACKGROUND

The present disclosure relates generally to sensors and methods for making the same.

Since the inception of semiconductor, technology, a consistent trend has been toward the development of smaller device dimensions and higher device densities. As a result, nanotechnology has seen explosive growth and generated considerable interest. Nanotechnology is centered on the fabrication and application of nano-scale structures, or structures having dimensions that are often 5 to 100 times smaller than conventional semiconductor structures. Nanowires are included in the category of nano-scale structures.

Nanowires are wire-like structures having diameters on the order of about 1 nm to about 100 nm. Nanowires are suitable for use in a variety of applications, including functioning as conventional wires for interconnection applications, as semiconductor devices, and as sensors. While holding much promise, the practical application of nanowires has been somewhat limited. In particular, non-suspended nanowire sensing devices tend to leak heat, and, in some instances, are incapable of sensing relatively small temperature changes.

BRIEF DESCRIPTION OF THE DRAWINGS

Features and advantages of embodiment(s) of the present disclosure will become apparent by reference to the following detailed description and drawings, in which like reference numerals correspond to similar, though not necessarily identical components. For the sake of brevity, reference numerals or features having a previously described function may not necessarily be described in connection with other drawings in which they appear.

DETAILED DESCRIPTION

Providing nanowires, especially nanowires with properties that can vary in response to chemical reactions, that can be integrated on a silicon platform, and that can be fabricated in production quantities for a reasonable cost has proven difficult.

Embodiment(s) of the sensor disclosed herein overcome one or more of the drawbacks discussed hereinabove, as they are advantageously capable of sensing the presence and/or quantity of a reaction (e.g., a chemical reaction). The sensors incorporate nanowire(s) grown laterally between two electrodes. The nanowires may advantageously have multiple segments of different conductivity types or different materials (e.g., different from other segments and/or different from the electrode materials). The connection between the various segments of the nanowire may advantageously be electrically useful (e.g., an ohmic connection, a junction (i.e., a diode), or the like).

A reaction occurring near the sensing material located at the connection between the various nanowire segments is capable of generating a measurable property. As used herein, the term "sensing material" refers to a material that has two discrete states (e.g., of the property to be measured), or a material that has more than two states, including a continuum of states (i.e., the material is continuously variable). The property may advantageously be used to determine the presence and/or quantity of the reaction, the concentration of the reaction reactants, or combinations thereof. Further, without being bound to any theory, it is believed that the species of the reaction reactants may be determined by selecting a coating that preferentially and/or selectively binds specific reactants or reaction products.

Using a nanowire to sense chemical reaction(s) may be advantageous, in part, because of the low thermal mass of the nanowire. It is believed that the low thermal mass increases the sensitivity to small amounts of reaction or small changes in the reaction, and decreases the response time for sensing the reaction or changes in the reaction. Furthermore, with suitable bias, both endothermic and exothermic reactions may be sensed.

Figure 1:
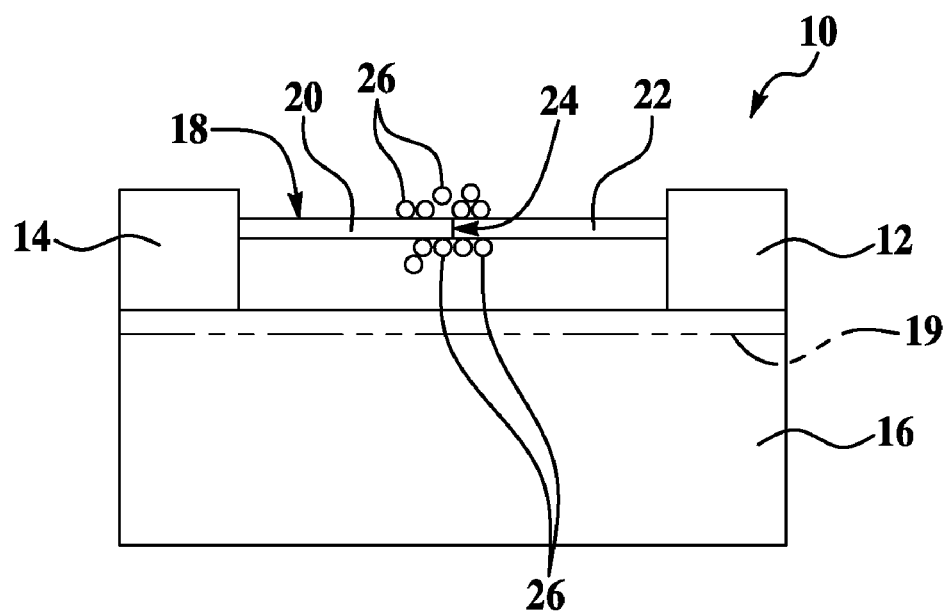
FIG. 1 is a schematic view of an embodiment of a sensor.

Referring now to FIG. 1, an embodiment of the sensor 10 includes two electrodes 12, 14 positioned on a substrate 16. In an embodiment, the electrodes 12, 14 are formed from a layer of silicon (Si) cut or polished with the surface plane being a (110) crystal lattice plane. Such a layer is referred to as a (110) oriented Si layer. As used herein, the (110) plane is considered to be horizontally oriented with respect to the Cartesian coordinate system. The (110) oriented layer from which the electrodes 12, 14 are formed further has (111) planes of the Si crystal lattice, at least some of which are approximately perpendicular to, and intersect with the horizontally oriented (110) surface. These intersecting (111) planes are referred to herein as vertically oriented (111) planes or surfaces, noting that the (111) planes are approximately vertically oriented relative to the horizontal (110) surface of the layer from which the electrodes 12, 14 are formed. The (110) Si layer may be etched anisotropically using an etchant, such as KOH. The (111) planes etch slowly compared to other crystal planes; as such, the resulting structure, which forms the electrodes 12, 14, is bounded by vertical (111) planes. These (111) planes form the sides of the electrodes 12, 14.

As used herein, the term "horizontal" generally refers to a direction or a plane that is parallel with a surface of the substrate 16 or wafer, while the term "vertical" generally refers to a direction or plane that is substantially or approximately perpendicular to the substrate surface. It is to be understood that the specific use of the terms "horizontal" and "vertical" to describe relative characteristics is to facilitate discussion and is not intended to limit embodiments of the present disclosure.

The electrodes 12, 14 may have first and second conductivity types. It is to be understood that the first and second conductivity types may be the same or different. In a non-limitative example, the first conductivity type is p-type conductivity, and the second conductivity type is n-type conductivity, or vice versa. In other embodiments, both the first and second conductivity types are p-type conductivity or n-type conductivity.

If the property to be measured is an electrical property, the electrodes 12, 14, are electrically isolated from each other except through a nanowire 18. If the substrate 16 is formed of an insulating material, the electrodes 12, 14, are electrically isolated from each other. If the substrate 16 is formed of a conductive or a semi-conductive material, an insulating layer 19 is established between the respective electrodes 12, 14, and the substrate 16 to electrically isolate the electrodes 12, 14 from each other.

The nanowire 18 is grown substantially laterally between the electrodes 12, 14. In an embodiment, growth of the nanowire 18 is initiated at one of the electrodes 12, 14, and a connection is formed at the other of the electrodes 14, 12. It is to be understood, however, that the nanowire 18 may be formed via any suitable method. A non-limitative example of forming a lateral nanowire 18 is described in U.S. patent application Ser. No. 10/738,176, filed on Dec. 17, 2003 (U.S. Publication No. 2005/0133476 A1, published Jun. 23, 2005), which is incorporated herein by reference in its entirety. Other example methods for forming lateral nanowires 18 are described in "Ultrahigh-density silicon nanobridges formed between two vertical silicon surfaces" by Islam et al., published in 2004 in volume 15 of *Nanotechnology* at pages L5-L8; and "A novel interconnection technique for manufacturing nanowire devices" by Islam et al., published in 2005 in volume 80 of *Appl. Phys. A* at pages 1133-1140.

As depicted, the nanowire 18 has at least two segments 20, 22. As the nanowire 18 grows, it may be doped with a dopant that is capable of introducing the first conductivity type or the second conductivity type to one or more of the nanowire segments 20, 22. Dopants for introducing p-type conductivity into group IV semi-conductors include, but are not limited to boron, other like elements, or combinations thereof; and dopants for introducing n-type conductivity into group IV semi-conductors include, but are not limited to phosphorus, arsenic, antimony, other like elements, or combinations thereof. Different dopants may be suitable for group III-V materials, such as, for example gallium arsenide.

In the embodiment shown in FIG. 1, one of the segments 20, 22 has the first conductivity type, and the other of the segments 22, 20 has the second conductivity type. Generally, the first and second conductivity types are different so that a junction (e.g., a p-n junction) is formed between the two segments 20, 22. In a non-limitative example, the first conductivity type is p-type conductivity, and the second conductivity type is n-type conductivity, or vice versa. If the semiconductor material forming both segments 20, 22 of the nanowire is the same material, the junction is a p-n homojunction.

In another embodiment, one of the segments 20, 22 is formed of a first material, and the other of the segments 22, 20 is formed of a second material that is different than the first material, so that a heterojunction is formed between the two segments 20, 22. The materials for the segments 20, 22 may be selected to be of opposite conductivity types so that a p-n heterojunction is formed, or they may be of the same conductivity type so that an isotype heterojunction is formed.

As a non-limiting example of the sensor 10 shown in FIG. 1, the nanowire 18 and electrodes 12, 14 may form a first conductivity type-first conductivity type-second conductivity type-second conductivity type structure, where the nanowire 18 has a second conductivity type segment (e.g., segment 22 adjacent a second conductivity type electrode 12) and a first conductivity type segment (e.g., segment 20 adjacent a first conductivity type electrode 14). A non-limitative example of such a structure is a p-type-p-type-n-type-n-type (p-p-n-n) structure, which has a p-p junction (at the electrode 14-segment 20 interface), a p-n junction (at the segment 20-segment 22 interface), and an n-n junction (at the segment 22-electrode 12 interface). The first conductivity type segment 20 of the nanowire 18 is grown from the electrode 14 of the first conductivity type. During growth of the nanowire 18, growth of the first conductivity type segment 20 may be stopped, and a second conductivity type segment 22 may be grown from the first conductivity type segment 20. The conductivity type may be changed by changing the dopant-containing species reaching the region where semiconductor material is being added to continue growth of the nanowire 18. Alternatively, the dopant can be added after growth of the nanowire 18 is complete. In the embodiment shown in FIG. 1, the second conductivity type segment 22 forms a connection with the electrode 12 of the second conductivity type. It is to be understood that the conductivity of the respective electrodes 12, 14 and segments 20, 22 may be altered as desired.

In the embodiment shown in FIG. 1, a junction 24 is formed at the interface of the nanowire segments 20, 22. As previously described, the junction 24 is often a homojunction. In some instances, though, the junction 24 is a heterojunction. In an embodiment, a sensing material 26 is positioned adjacent to the junction 24 and adjacent to at least a portion of each of the nanowire segments 20, 22. It is to be understood that the sensing material 26 may also be positioned adjacent to other portions of the nanowire segments 20, 22. The sensing material 26 may be applied to the nanowire 18 via vapor deposition techniques, liquid deposition techniques (including self-assembling of a monolayer), inkjet deposition techniques, or the like, or combinations thereof. It is to be understood that the sensing material 26 may be positioned on, under, and/or so it substantially surrounds the junction 24 and the segment 20, 22 portions.

As previously described, the sensing material 26 may have two discrete states (between which the material 26 is switchable), or it may have more than two states, including a continuum of states. The two discrete states may be of the property to be measured, for example, a high resistance state and a low resistance state. The two discrete states may represent "ON" and "OFF" states. In this embodiment, upon exposure to a certain reaction property, the sensing material 26 turns from ON to OFF or from OFF to ON. Generally, sensing materials 26 having two discrete states are suitable for measuring the presence or absence of a reaction, and sensing materials 26 with more than two states or a continuum of states are suitable for measuring an amount of the reaction.

The sensing material 26 may be a material that is switchable between at least a high and a low resistance state, a plurality of nanoparticles coated with spacer ligands, or combinations thereof. As a non-limiting example, the sensing material 26 may be a material that has a high resistance state and a low resistance state, and is switchable from one state to the other state when exposed to conditions that induce resistance changes (e.g., the reaction being measured). As another non-limiting example, the sensing material 26 may be a material with a continuum of states so that its resistance is a continuous function of temperature. In this case, the resistance measured indicates the temperature of the material and, therefore, the intensity of the reaction at any instant of time. By integrating the changes over time, the quantity of the reaction that has occurred can be measured.

The embodiment shown in FIG. 1 depicts the plurality of nanoparticles coated with spacer ligands as the sensing material 26. A reaction (e.g., chemical or otherwise) may be generated at or near the junction 24 of the sensor 10. In an embodiment, heat is generated by the reaction. In a non-limiting example, the nanoparticles shown in FIG. 1 expand upon exposure to the generated heat, causing the spacing between the nanoparticles to decrease. This decreased space lowers the resistance of a path in parallel with the junction 24.

In a non-limiting example, the nanoparticles may act as a binary sensing material that undergoes a Mott transition (switches from a nonconductive or "OFF" state to a conductive or "ON" state) when exposed to heat that is generated, for example, from such a reaction (e.g., chemical or otherwise). As such, the heat and/or the change in resistance is indicative of the chemical reaction occurring near the junction 24. In this embodiment, the resistance may be measured, and such measurements may be used to determine the presence of the reaction, the concentration of the reaction reactants, or combinations thereof.

Very generally, the change of resistance of the sensing material 26 shown in FIG. 1 depends, at least in part, on the temperature, and consequently on the amount of heat generated by the reaction. The amount of heat generated depends, at least in part, on the quantity of the reaction, and therefore on the concentration of the reactants. If the change is abrupt, the presence of a reaction is detectable. If however, the change is gradual with temperature, the reaction presence and the reactants' concentration are detectable.

Embodiments of the sensor 10 having a junction may be biased so the current flowing through the nanowire 18 is less than the current carried by the sensing material 26 in its conductive state. The junction may be reverse biased, or biased with a low forward bias so that the current flow through the junction 24 is low. A change in the parallel conductance through the sensing material 26 is then readily measured between the electrodes 12, 14.

Figure 2:
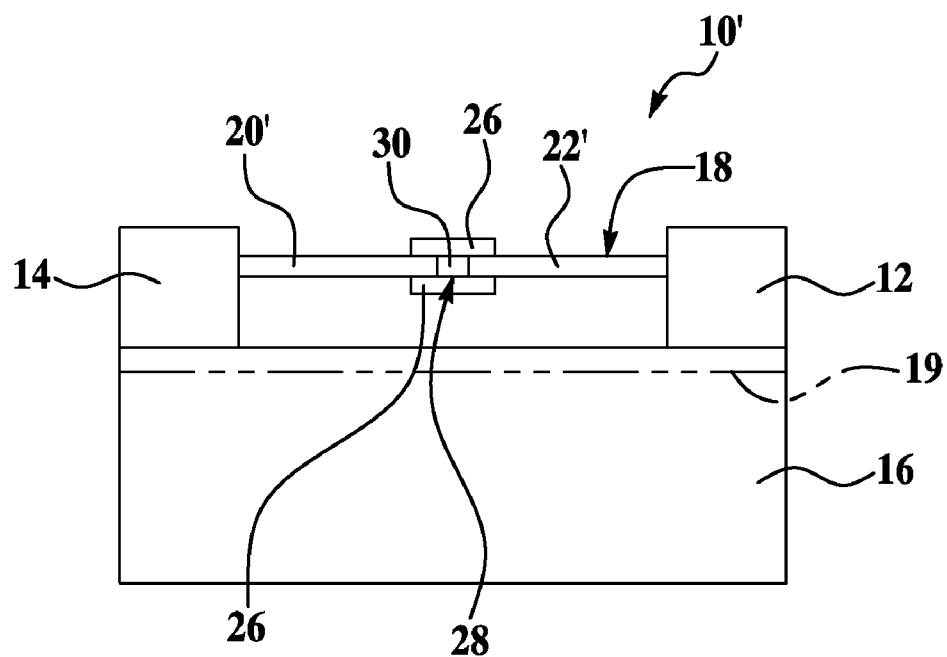
FIG. 2 is a schematic view of another embodiment of a sensor.

Referring now to FIG. 2, another embodiment of a sensor is generally depicted at 10'. The substrate 16 and electrodes 12, 14 described in reference to FIG. 1 are suitable for use in the embodiment of the sensor 10' shown in FIG. 2.

In this embodiment, the nanowire 18 is grown substantially laterally between the electrodes 12, 14, and includes at least two segments 20', 22' having a connection 28 therebetween. It is to be understood that the nanowire 18 is formed via embodiments of the methods disclosed hereinabove. Generally, the nanowire segments 20', 22' in this embodiment are selected from metals, semi-conductor materials, or combinations thereof. Non-limiting examples of such materials include silicon, germanium, indium phosphide, gallium arsenide, boron, gold, or the like, or combinations thereof.

The nanowire 18 depicted in FIG. 2 also includes an insulating material 30 located at the connection 28 between the segments 20', 22'. The insulating material 30 may be grown as a segment of the nanowire 18 by changing the gaseous species to which the catalyzing nanoparticle (which forms the nanowire 18) is exposed. Non-limiting examples of the insulating material 30 include gallium aluminum arsenide, or the like.

In the embodiment shown in FIG. 2, the sensing material 26 is positioned adjacent to: the connection 28; the insulating material 30; and at least a portion of each of the segments 20', 22'. It is to be understood that the sensing material 26 may also be positioned adjacent to other portions of the nanowire segments 20', 22'. The sensing material 26 may be established via any of the techniques described hereinabove. It is to be understood that the sensing material 26 may be positioned on, under, and/or so it substantially surrounds the connection 28, the insulating material 30, and the portions of segments 20', 22'.

As previously described, the sensing material 26 may be a resistive material that is changeable between at least a high and a low resistance state, a plurality of nanoparticles coated with spacer ligands, or combinations thereof. The embodiment shown in FIG. 2 depicts the resistive material that is switchable between the high and low resistance states.

Similar to the embodiment of the sensor 10 shown in FIG. 1, a reaction (e.g., chemical or otherwise) may be generated at or near the connection 28 of the sensor 10'. The resistance of sensing material 26 changes to a different state upon exposure to at least some measurable property (e.g., heat, temperature increase or decrease, etc.) generated by the reaction. This exposure results in a change in the resistance of a path in parallel with the connection 28. Depending, at least in part, on the property and amount generated during the reaction, the resistance may be increased or decreased. Furthermore, the exposure to the measurable property may cause the material 26 to switch from one resistance state to another (generally suitable for detecting presence of a reaction), or to move through more than two states or a continuum of states of different resistance (generally suitable for detecting reaction presence and the reactants' concentration).

For an exothermic reaction, the resistance of the sensing material 26 shown in FIG. 2 usually decreases to a lower state upon exposure to at least some measurable property generated by the reaction. This results in a decrease in the resistance of a path in parallel with the connection 28.

The change in resistance is indicative of the chemical reaction occurring near the connection 28. The resistance may be measured, and such measurements may be used to determine the presence and/or quantity of the reaction, the concentration of the reaction reactants, the species of the reaction reactants, or combinations thereof.

For the embodiments of the sensor 10, 10' disclosed herein, the nanowire 18 may include a junction 24 between differently doped segments 20, 22, of the same material, a junction 24 between segments 20, 22, of different materials, or an insulating material 30 between two conducting segments 20', 22'. The sensing material 26 may include materials that are capable of switching between two states, or moving between more than two states or through a continuum of states. The sensors 10, 10' shown in FIGS. 1 and 2 are non-limiting examples, and it is to be understood that different combinations of the nanowire 18 and sensing material 26 are considered to be within the purview of the present disclosure.

While several embodiments have been described in detail, it will be apparent to those skilled in the art that the disclosed embodiments may be modified. Therefore, the foregoing description is to be considered exemplary rather than limiting.

What is claimed is:

1. A sensor, comprising:
   at least two electrodes;
   at least one nanowire having at least two segments extending substantially laterally between the at least two electrodes, whereby a junction or connection is formed between the at least two segments; and
   a sensing material having at least two states positioned adjacent to the junction or connection, and adjacent to at least a portion of each of the at least two segments.

2. The sensor as defined in claim 1 wherein the sensing material is selected from a material having a resistance changeable between at least a high and a low resistance state, a plurality of nanoparticles coated with spacer ligands, and combinations thereof.

3. The sensor as defined in claim 1 wherein the sensing material has more than two states, including a continuum of states.

4. The sensor as defined in claim 1, further comprising an insulating material established between the at least two segments at the connection, wherein the sensing material is positioned adjacent to the insulating material and at least a portion of each of the at least two segments.

5. The sensor as defined in claim 4 wherein the at least two segments are formed of a conductive material selected from metals and semiconductor materials.

6. The sensor as defined in claim 4 wherein the sensing material is selected from a material having a resistance changeable between at least a high resistance state and a low resistance state, a plurality of nanoparticles coated with spacer ligands, and combinations thereof.

7. The sensor as defined in claim 1 wherein one of the at least two segments has a first conductivity type or is formed of a first material, and an other of the at least two segments has a second conductivity type or is formed of a second material that is different from the first material.

8. The sensor as defined in claim 7 wherein the first conductivity type is one of a p-type and an n-type, and wherein the second conductivity type is an other of the n-type and the p-type.

9. The sensor as defined in claim 7 wherein the sensing material is selected from a material having a resistance changeable between at least a high resistance state and a low resistance state, a plurality of nanoparticles coated with spacer ligands, and combinations thereof.

10. A sensing method, comprising:
exposing a sensing material having at least two states to a reaction, the sensing material being positioned adjacent to a junction or connection formed between at least one nanowire having at least two segments and adjacent to at least a portion of each of the at least two segments, the at least one nanowire extending laterally between at least two electrodes, wherein the exposing generates a measurable property; and
detecting the measurable property.

11. The method as defined in claim 10 wherein the measurable property is heat, temperature, resistance, or combinations thereof.

12. The method as defined in claim 11 wherein the measurable property causes a change in a resistance path that is in parallel with the junction or connection.

13. The method as defined in claim 10 wherein the measurable property is indicative of the presence of a chemical reaction, the absence of a chemical reaction, a quantity of the chemical reaction, or combinations thereof.

14. The method as defined in claim 10 wherein the sensing material is selected from a material having a resistance changeable between at least a high resistance state and a low resistance state, a plurality of nanoparticles coated with spacer ligands, and combinations thereof.

15. The method as defined in claim 14 wherein the sensing material includes the plurality of nanoparticles coated with spacer ligands, and wherein the sensing material undergoes a Mott transition when exposed to heat.

* * * * *